United States Patent
Luciano et al.

(10) Patent No.: US 6,866,558 B2
(45) Date of Patent: Mar. 15, 2005

(54) ADJUSTABLE APPARATUS FOR SUPPORTING MILK EXTRACTION DEVICES

(75) Inventors: Catherine Luciano, Boca Raton, FL (US); Laurie Zanotti, Hartland, WI (US)

(73) Assignee: Made by Moms, Inc., Hartland, WI (US)

( * ) Notice: Subject to any disclaimer, the term of this patent is extended or adjusted under 35 U.S.C. 154(b) by 3 days.

(21) Appl. No.: 10/378,318

(22) Filed: Mar. 3, 2003

(65) Prior Publication Data

US 2003/0199224 A1 Oct. 23, 2003

Related U.S. Application Data

(63) Continuation-in-part of application No. 09/920,472, filed on Aug. 1, 2001, now abandoned.

(51) Int. Cl.[7] .............................................. A41C 3/00
(52) U.S. Cl. ........................................ 450/36; 450/58
(58) Field of Search ..................... 450/36, 37, 7–10, 450/15–18, 65–67, 79, 82, 58; 2/104–106, 113–115, 69; 604/73–76, 118–119

(56) References Cited

U.S. PATENT DOCUMENTS

| | | | | |
|---|---|---|---|---|
| 407,341 A | * | 7/1889 | Ferris | 450/18 |
| 513,086 A | * | 1/1894 | Chambers | 450/58 |
| 1,189,589 A | * | 7/1916 | Lawrence | 450/36 |
| 2,502,524 A | * | 4/1950 | Keller | 450/37 |
| 3,826,266 A | * | 7/1974 | Alpert | 450/11 |
| 6,004,186 A | * | 12/1999 | Penny | 450/36 |
| 6,213,840 B1 | * | 4/2001 | Han | 450/36 |
| 6,227,936 B1 | * | 5/2001 | Mendoza | 450/36 |
| 6,247,996 B1 | * | 6/2001 | Fields | 450/36 |

* cited by examiner

*Primary Examiner*—Gloria Hale
(74) *Attorney, Agent, or Firm*—Gehrke & Associates, s.c.

(57) ABSTRACT

An interface jig for removably securing a portable auger to a vehicle includes a carriage guide assembly, a sliding carriage assembly and a receiver assembly. The carriage guide assembly includes a vertical support having an upper portion and a bottom portion. A hitch adapter is affixed to the bottom portion to secure the carriage guide assembly to a vehicle hitch. The sliding carriage assembly includes a horizontal member having a first end opposite a second end. The first end is affixed to a vertical member that slides along the vertical support between the upper portion and the lower portion of the carriage guide. The receiver assembly is attached to the second end of the sliding carriage assembly.

17 Claims, 4 Drawing Sheets

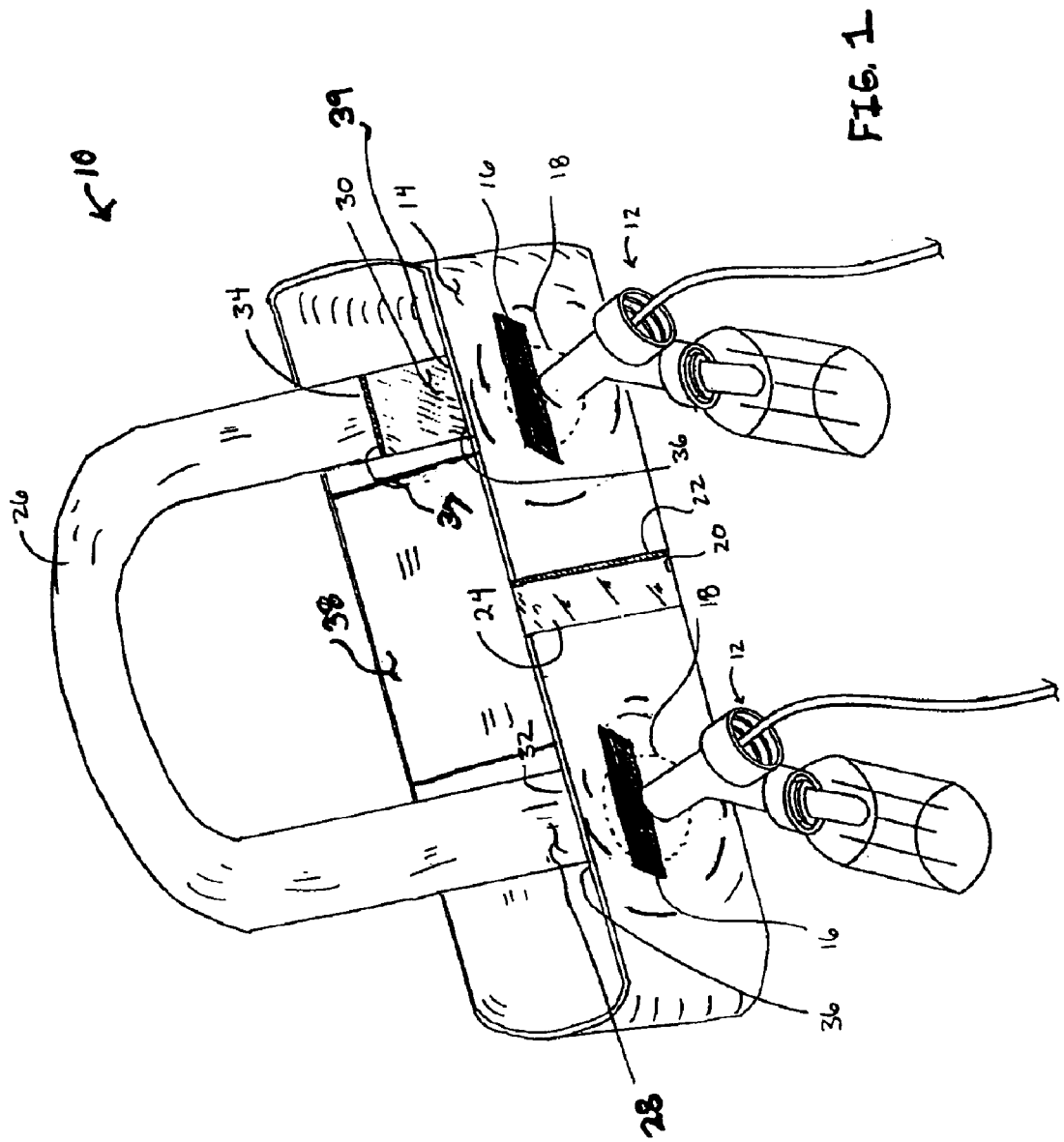

ADJUSTABLE APPARATUS FOR SUPPORTING MILK EXTRACTION DEVICES

Cross-Reference to Related Applications: This application is a continuation-in-part application of U.S. patent application Ser. No. 09/920,472 filed on Aug. 1, 2001 now abandoned.

BACKGROUND OF THE INVENTION

1. Field of the Invention

This invention is in the field of breastfeeding, specifically relating to an adjustable "one-size-fits-all" apparatus fitted around a woman's breasts to aid in the mechanical extraction of breast milk using one or multiple milk extraction suction devices.

2. Description of the Related Art

For the sake of convenience, this patent specification will focus on simultaneously pumping both breasts using two separate milk extraction devices, but it is understood that the problems addressed and solutions presented by the present invention are also applicable to extracting milk using a single milk extraction device (e.g., nursing a baby on one breast while simultaneously pumping the other breast) or pumping each breast separately.

A breast pump includes suction cup devices that are secured to the nipples of the mother's breasts. Tubes connect the suction devices to the breast pump and a motor in the pump typically creates varying degrees of suction between the suction devices and the breasts. The suction extracts breast milk from the breasts into a pair of bottles attached to the suction devices. The mother maintains the suction by manually pressing the suction devices against the breasts throughout the pumping procedure. This is often a time consuming and frustrating process as the mother must maintain a particular position for a long period of time without any use of her hands.

Despite this frustration, it has become increasingly common for working mothers to choose to maintain a breastfeeding relationship with their child by using electric, battery or manual breast pumps to extract milk several times a day while at work. While the breast pumps are able to extract milk, they still are not nearly as efficient as a nursing baby. Therefore, several companies have set up separate rooms and policies to help nursing mothers maintain the breastfeeding relationship with their child. In this regard, one of the keys to maintaining a breastfeeding relationship is the ability of the nursing mother to relax and quickly experience the let-down reflex. This is difficult to achieve while concentrating on maintaining proper suction by using both hands to press each of the suction devices against the breasts.

Additionally, nursing mothers often find themselves in situations where they have to pump in front of other people. In this regard, it would be useful to provide the nursing mother with a means to cover her breasts while she is pumping. It would also be useful to provide the nursing mother with a pumping device that is easily adjusted in the front for easy access. To maximize comfort and fit, it would also be useful to provide the nursing mother with a pumping device that adjusts in both the front and the back to accommodate the nursing mother's varying chest measurement while also accommodating for the placement of the covered slits that align with the mother's breasts.

A device that would allow a breastfeeding mother to have full use of her hands during each of the pumping sessions would allow the mother to relax and even perform other tasks while pumping. It is critical that such a device be capable of providing adequate pressure between the suction device and the breasts to adequately and efficiently empty the breasts. Unfortunately, current devices adapted to allow a nursing mother "hands free" pumping simply do not work, as they are unable to maintain proper suction between the suction devices and the breasts.

Moreover, several of these devices require the assembly and disassembly of several complicated attachments to hold the suction devices in place. These devices are typically very expensive and still ineffective at maintaining the proper suction between the devices and the breasts, thereby allowing hands free pumping. Finally, these devices also may require permanent alteration of the nursing brassiere, thereby rendering it ineffective for nursing the baby in that after the attachments are secured to the brassiere, the brassiere can only be used as a pumping aid.

SUMMARY OF THE INVENTION

Accordingly, one object of this invention is to provide an apparatus for supporting milk extraction devices that includes an elongated band that is adjusted to frictionally engage a woman's breasts, a pair of slits, a front adjustment and a back adjustment. The pair of slits is formed in the band, and each of the slits is positioned proximate the woman's breasts and configured to support a milk extraction device therethrough. The front adjustment is located between the pair of slits and the back adjustment is located opposite the front adjustment.

Yet another object of this invention is to provide an apparatus for supporting milk extraction devices including an elongated band that is adjusted to frictionally engage a woman's breasts, a pair of covered slits, a front adjustment and a back adjustment. The pair of covered slits is formed in the elongated band, and each of the covered slits is positioned proximate the woman's breasts and configured to support a milk extraction device therethrough. The front adjustment is located between the pair of covered slits, and the back adjustment is located opposite the front adjustment.

Yet another object of this invention is to provide an apparatus for supporting milk extraction devices including an elongated band that is adjusted to frictionally engage a woman's breasts, a pair of slits, a front closure and a back closure. The pair of slits is formed in the elongated band, and each of the slits is positioned proximate the woman's breasts and configured to support a milk extraction device therethrough. The front closure is formed in the elongated band and located between the pair of slits. The back closure is located opposite the front closure and positioned proximate the woman's back.

BRIEF DESCRIPTION OF THE DRAWINGS

Preferred exemplary embodiments of the invention are illustrated in the accompanying drawings in which like reference numerals represent like parts throughout, and in which:

FIG. 1 is a perspective view of a halter apparatus according to the present invention;

DETAILED DESCRIPTION OF THE PREFERRED EMBODIMENTS

Figure 4:
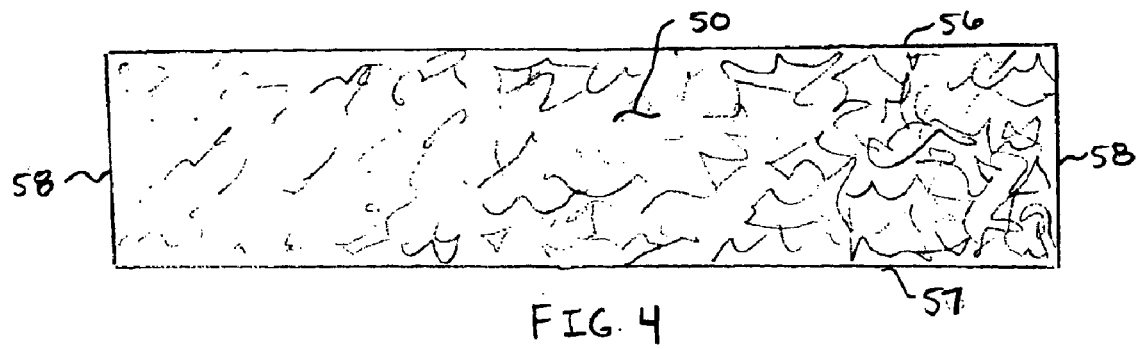
FIG. 4 is a rear view of the back adjustment strap according to the present invention.

Referring to FIG. 1, an apparatus 10 for supporting a pair of milk extraction devices 12 includes an elongated band 14 that is adjusted to frictionally engage and wrap around a nursing mother's breasts. A pair of covered slits 16 is formed in elastic band 14 and each of the covered slits is aligned with the nipple portion of each breast. Covered slits 16 support a circular suction cup 18 (dotted lines) of milk extraction device 12. In the preferred embodiment of the current invention, each slit is approximately 3–6 inches in length (e.g., 4½ inches). Elongated band 14 is manufactured as a "one-size-fits-all" device. In this regard, elongated band 14 is fully adjustable to fit a wide range of chest measurements and cup sizes.

Each covered slit 16 is a button-hole type of collapsible opening that alternates between a closed position when milk extraction devices 12 are not supported by covered slits 16 and a partially opened position when milk extraction devices 12 are supported by covered slits 16.

In the preferred embodiment of the current invention, band 14 is an elastic-type band that is approximate 3 to 10 inches in width. In the alternative, band 14 may be constructed by covering a piece of elastic with a stretchable material. In this regard, band 14 may alternatively be manufactured with a non-stretchable woven or non-woven material (e.g., terry cloth, rayon, polyester, etc.).

As discussed above, band 14 is configured to adapt to varying chest and cup sizes with a temporary front closure means 20 and a temporary back closure means 38 known in the art (e.g., VELCRO® hook and loop fastener closures, button and button holes, hook and eye closures, snaps, tied fabric extensions, etc.). In the preferred embodiment of the current invention, a first end 22 of band 14 is removably attached to a second end 24 of band 14 using mating strips of VELCRO® hook and loop strips located in front of the nursing mother. In the alternative, band 14 may be manufactured to accommodate varying chest and cup sizes consistent with industry standards (e.g., small, medium, large, extra-large) or custom fit.

Temporary front closure means 20 is used to adjust the friction between elongated elastic band 14 and the woman's breasts. As illustrated in FIG. 1, front closure 20 is located between covered slits 16 to provide easy adjustment of band 14 for adequate friction to support milk extraction devices 12 and to align covered slits 16 with the woman's breasts.

In an alternative embodiment of the current invention, band 14 may be manufactured as a single tubular shape having permanently secured ends to form a continuous piece of fabric. The ends may be secured with methods that are well-known in the art (e.g., heat-activated fusible material, fabric adhesive, thread, etc.).

Apparatus 10 further includes a halter-type neck strap 26 with a first strap portion 28 and a second strap portion 30. First strap portion 28 further includes a first end 32 and a second end 34. First end 32 of first strap portion 28 is attached to elongated band 14 proximate one of covered slits 16.

Halter-type neck strap 26 is constructed by covering an elastic-type band (e.g., 1 to 3 inches in width) with a stretchable material. Alternatively, neck strap 26 may be manufactured with a non-stretchable woven or non-woven material (e.g., terry cloth, rayon, polyester, etc.). Neck strap 26 is approximately 25 to 35 inches in length.

In the preferred embodiment of the present invention, first end 32 of first strap portion 28 is permanently attached to elongated band 14 at a top portion 36 of elongated band 14. Second end 34 of first strap portion 28 is temporarily attached to a first end 37 of second strap portion 30 using adjusting means (e.g., mating strips of VELCRO® hook and loop strips attached to second end 34 and first end 37 ). A second end 39 of second strap portion 30 is permanently attached to elongated band 14 at top portion 36 of elongated band 14 proximate one of covered slits 16.

Alternatively, one or both of first end 32 of first strap portion 28 and second end 39 of second strap portion 30 may be temporarily attached to top portion 36 of elongated strap 14 using adjusting means that are well-known in the art (e.g., mating VELCRO® hook and loop strips).

In yet another alternative embodiment of the present invention, neck strap 26 may be manufactured from a single piece of material that having two ends that are attached to top portion 36 proximate each of slits 16 either permanently or temporarily (e.g., using a VELCRO® hook and loop closure). In the preferred and alternative configurations, neck strap 26 wraps behind the neck and is adjusted using adjusting means located in front of the nursing mother.

In operation, a nursing mother wraps elongated elastic band 14 around her chest, aligns covered slits 16 with her breasts, and obtains a tight fit using front closure means 20 and back closure means 38. To provide further comfort, the nursing mother may also place neck strap 26 behind her neck and adjust the position of strap 26 by changing the position of second end 34 in relation to first end 37.

Circular suction cups 18 of milk extraction devices 12 are inserted through covered slits 16 and elongated band 14 may be adjusted to ensure proper friction between cups 18 and the woman's breasts. Thereafter, the nursing mother turns on the breast pump and is able to maintain a comfortable position while extracting milk and having full use of both of her hands. At the end of the pumping session, the nursing mother turns off the breast pump, easily removes cups 18 from covered slits 16, and removes elastic band 14 from her breasts.

Figure 2:
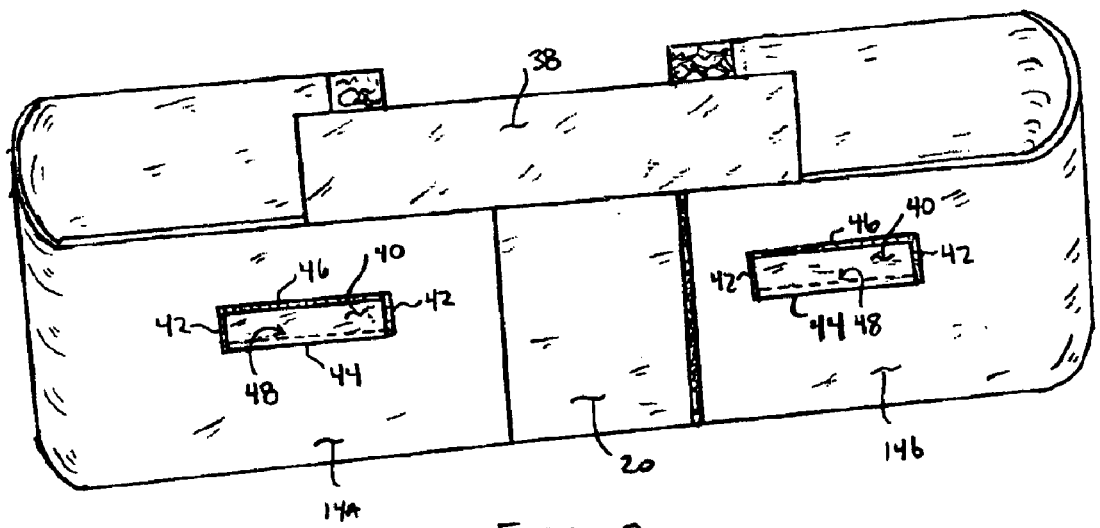
FIG. 2 is a front view of a pumping band according to the present invention.

FIG. 2 illustrates a first elastic panel 14a, a second elastic panel 14b and back closure means 38. Button-hole type slits 48 each include a slit cover 40 having a pair of secured ends 42, a secured top edge 46 and an unsecured bottom edge 44. Suction cups 18 of milk extraction devices 12 are placed under slit cover 40 by lifting bottom edge 44 and inserted into slits 16.

Figure 3:
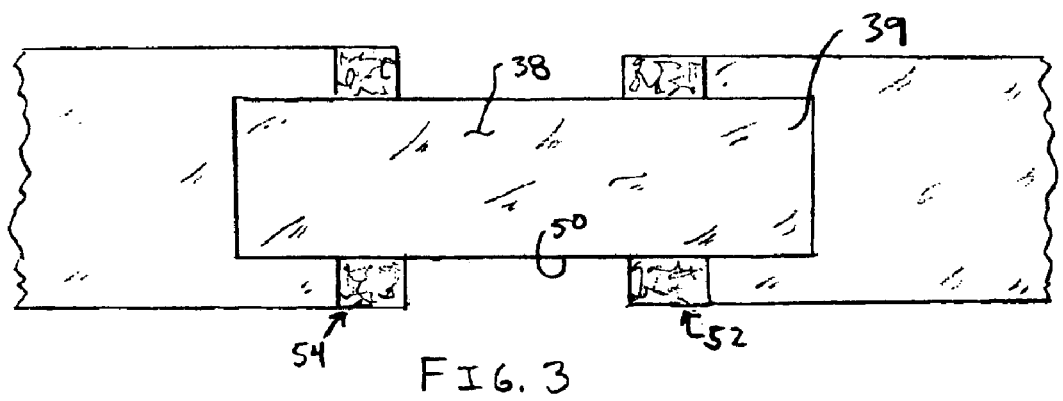
FIG. 3 is a perspective view of a back adjustment strap according to the present invention.

FIGS. 3–4 illustrates back closure means 38 having a front surface 39 and a back surface 50. In the preferred embodiment of the present invention, back surface includes a VELCRO® hook and loop closure that matingly engages VELCRO® hook and loop closure 52 on second panel 14b and VELCRO® hook and loop closure 54 on first panel 14a. Back closure 38 includes a top edge 56, a bottom edge 57 and ends 58. Closure 38 is preferably manufactured with a width 58 that is smaller than the width of panels 14a, 14b.

In the alternative, the width of closure 38 can be the same or larger than the width of panels 14a, 14b, and one end of closure 38 may be permanently attached to one of the ends of panel 14a or 14b. Back surface 50 is preferably manufactured using material that mates with hook-type material found on closures 52 and 54.

Figure 5:
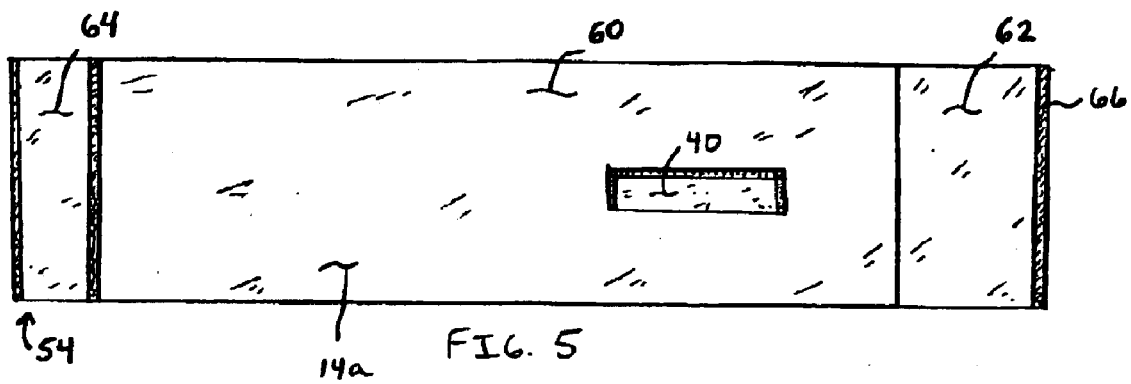
FIG. 5 is a front view of a first strap according to the present invention.
Figure 6:
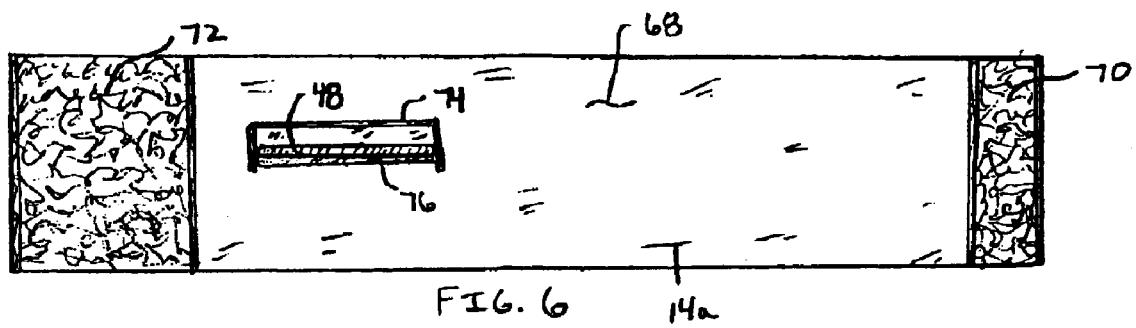
FIG. 6 is a rear view of the first strap according to the present invention.
Figure 7:
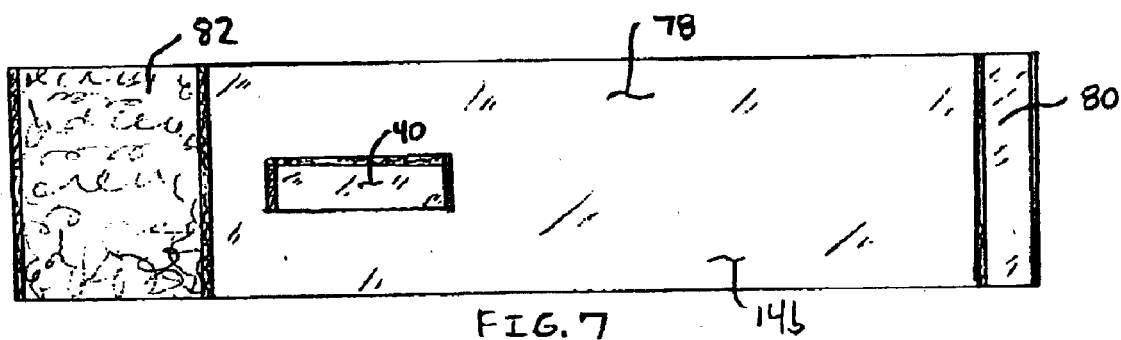
FIG. 7 is a front view of a second strap according to the present invention.
Figure 8:
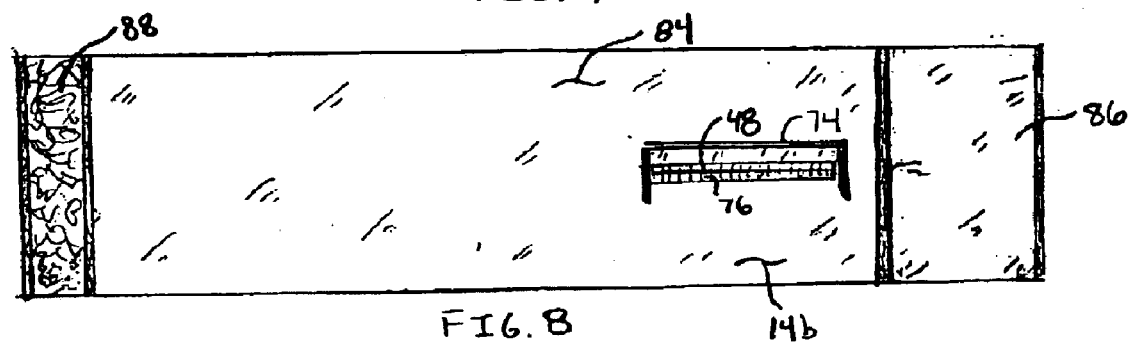
FIG. 8 is a back view of the second strap according to the present invention.

FIGS. 5–6 illustrate both sides of first panel 14a and FIGS. 7–8 illustrate both sides of second panel 14b. First panel 14a includes slit cover 40 over slit 48, a front surface 60 having closure surface 62, a front surface 64 of closure 54, and a finished edge 66. A back surface 68 of first panel 14a includes a fuzzy surface 72 that mates with a hook-type surface 82 of second panel 14b, and a hook surface 70 that mates with back fuzzy surface 50 of back closure means 38. Slit 48 is surrounded by a closure stitch 74 to hold slit cover 40 in place and a button-hole finish 76.

Second panel 14b includes slit cover 40 over slit 48, a front surface 78 having a hook closure surface 82 that matingly engages fuzzy surface 72 of panel 14a, and a front surface 80. A back surface 84 of second panel 14b includes a closure surface 86 and a hook surface 88 that mates with back fuzzy surface 50 of back closure means 38.

Figure 9:
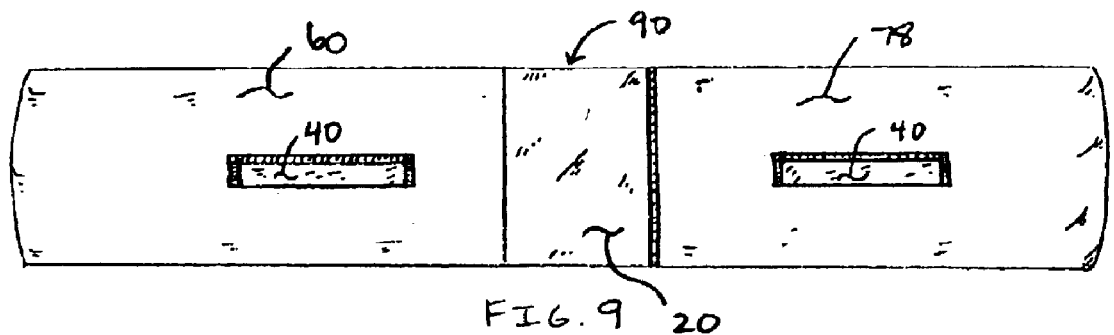
FIG. 9 is a front view of the pumping band including the covered slits according to the present invention.
Figure 10:
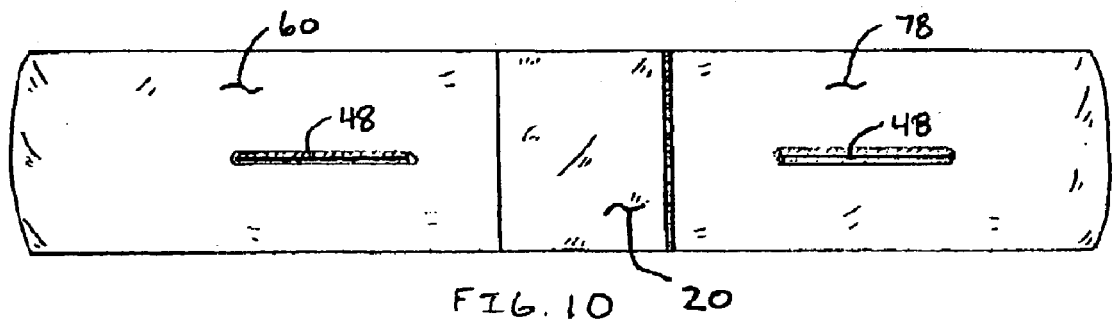
FIG. 10 is a front view of the pumping band illustrating uncovered slits according to the present invention.
Figure 11:
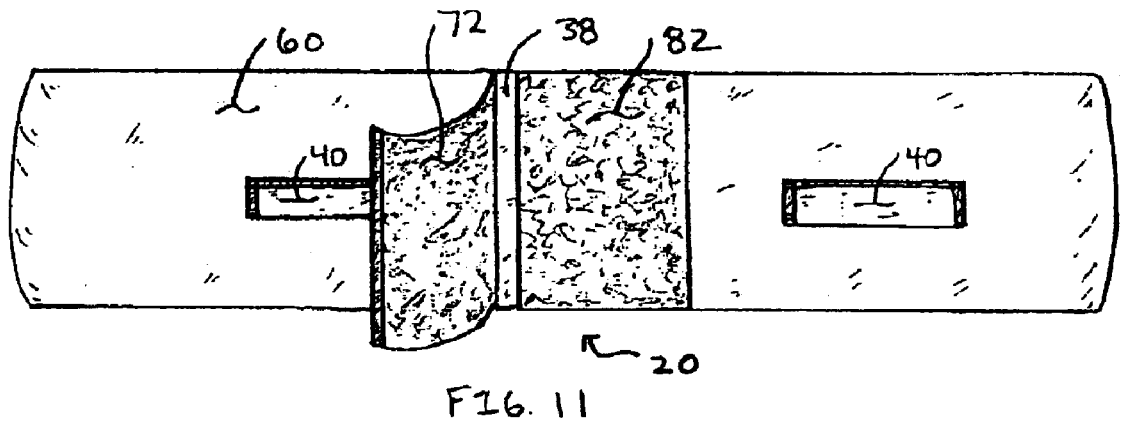
FIG. 11 is a front view of the pumping band illustrating an open front adjustment area according to the present invention.

FIGS. 9–10 further illustrate slit cover 40 and slit 48. Front closure 20 is in a closed position 90. FIG. 10 illustrates slit 48 with cover 40 removed. Additionally, FIG. 10 illustrates front surface 60 and front surface 78. FIG. 11 illustrates front closure 20 in an open position.

Many changes and modifications may be made to the invention without departing from the spirit thereof. The scope of some of these changes has already been discussed in relation to using other attachment and adjusting means for fastening various portions of elastic band 14 to one another. The scope of other changes will become apparent from the attached claims.

What is claimed is:

1. An apparatus for supporting milk extraction devices comprising:
   an elongated band that is adjusted to frictionally engage a woman's breasts including a first strap having a front closure portion and a back closure portion, a second strap having a front closure portion that engages the front closure portion of the first strap and a back closure portion, and a third strap that engages the back closure portion of the first strap and the back closure portion of the second strap; and
   a pair of covered slits formed in the elongated band, wherein each of the covered slits is positioned proximate the woman's breasts and configured to support a milk extraction device therethrough.

2. The apparatus according to claim 1, wherein the back closure portion of the first strap is permanently attached to the third strap.

3. The apparatus according to claim 2, wherein the back closure portion of the second strap is permanently attached to the third strap.

4. The apparatus according to claim 1, wherein the back closure portion of the first strap and the back closure portion of the second strap removably engages the third strap.

5. The apparatus according to claim 1, wherein each of the covered slits is a collapsible opening that alternates between a closed position when the milk extraction device is not supported by the slit and a partially opened position when the milk extraction device is supported by the slit.

6. The apparatus according to claim 1, further comprising a neck strap having a first portion and a second portion, wherein a first end of the first portion and a second end of the second portion are attached proximate each of the covered slits in the band, and a second end of the first portion is attached to a first end of the second portion.

7. The apparatus according to claim 6, wherein the first end of the first portion of the neck strap and the second end of the second portion of the neck strap are permanently attached to the elongated band and the second end of the first portion is temporarily attached to the first end of the second portion.

8. An apparatus for supporting milk extraction devices comprising:
   an elongated band that is adjusted to frictionally engage a woman's breasts including a first strap having a front closure portion and a back closure portion, a second strap having a front closure portion that engages the front closure portion of the first strap and a back closure portion, and a third strap that removably engages the back closure portion of the first strap and the back closure portion of the second strap; and
   a pair of covered slits formed in the elongated band, wherein each of the covered slits is positioned proximate the woman's breasts and configured to support a milk extraction device therethrough.

9. The apparatus according to claim 8, wherein each of the covered slits is a collapsible opening that alternates between a closed position when the milk extraction device is not supported by the slit and a partially opened position when the milk extraction device is supported by the slit.

10. The apparatus according to claim 8, further comprising a neck strap having a first portion and a second portion, wherein a first end of the first portion and a second end of the second portion are attached proximate each of the covered slits in the band, and a second end of the first portion is attached to a first end of the second portion.

11. The apparatus according to claim 10, wherein the first end of the first portion of the neck strap and the second end of the second portion of the neck strap are permanently attached to the elongated band and the second end of the first portion is temporarily attached to the first end of the second portion.

12. An apparatus for supporting milk extraction devices comprising:
   an elongated band that is adjusted to frictionally engage a woman's breasts including a first strap having a front closure portion and a back closure portion, a second strap having a front closure portion that removably engages the front closure portion of the first strap and a back closure portion, and a third strap that removably engages the back closure portion of the first strap and the back closure portion of the second strap; and
   a pair of covered slits formed in the elongated band, wherein each of the covered slits is positioned proximate the woman's breasts and configured to support a milk extraction device therethrough, and wherein each of the covered slits is a collapsible opening that alternates between a closed position when the milk extraction device is not supported by the covered slit and a partially opened position when the milk extraction device is supported by the covered slit.

13. The apparatus according to claim 12, further comprising a neck strap having a first portion and a second portion, wherein a first end of the first portion and a second end of the second portion are attached proximate each of the covered slits in the band, and a second end of the first portion is attached to a first end of the second portion.

14. The apparatus according to claim 13, wherein the first end of the first portion of the neck strap and the second end of the second portion of the neck strap are permanently attached to the elongated band and the second end of the first portion is temporarily attached to the first end of the second portion.

15. The apparatus according to claim 12 where the front closure of the first strap and the front closure of the second strap further include hook and loop fasteners to engage each other.

16. The apparatus according to claim 12, wherein the front closure of the first strap and the front closure of the second strap further include a zipper to engage each other.

17. The apparatus according to claim 12, wherein the back closure of the first strap and the back closure of the second strap each removably engage the third strap with hook and loop fasteners attached to the back closures and the third strap.

\* \* \* \* \*

UNITED STATES PATENT AND TRADEMARK OFFICE
CERTIFICATE OF CORRECTION

PATENT NO.        : 6,866,558 B2                                    Page 1 of 1
APPLICATION NO.   : 10/378318
DATED             : March 15, 2005
INVENTOR(S)       : Luciano et al.

It is certified that error appears in the above-identified patent and that said Letters Patent is hereby corrected as shown below:

On the cover page, column 2, please replace the printed ABSTRACT in its entirety with the following ABSTRACT paragraph:

-- An apparatus for supporting milk extraction devices includes an elongated band that is adjusted to frictionally engage a woman's breasts, a pair of slits, a front adjustment and a back adjustment. The pair of slits is formed in the band, and each of the slits is positioned proximate the woman's breasts and configured to support a milk extraction device therethrough. The front adjustment is located between the pair of slits and the back adjustment is located opposite the front adjustment. --

Signed and Sealed this
Twenty-eighth Day of August, 2012

David J. Kappos
*Director of the United States Patent and Trademark Office*